United States Patent
Natarajan et al.

(10) Patent No.: US 10,278,701 B2
(45) Date of Patent: May 7, 2019

(54) ADHESIVE STRUCTURE WITH TISSUE PIERCING PROTRUSIONS ON ITS SURFACE

(71) Applicants: Ethicon, Inc., Somerville, NJ (US); Agency for Science Technology and Research, Connexis (SG)

(72) Inventors: Sriram Natarajan, Hillsborough, NJ (US); Joseph J. Hammer, Hillsborough, NJ (US); Kevin Cooper, Flemington, NJ (US); Murty Vyakarnam, Bridgewater, NJ (US); Hong Yee Low, Botannia (SG); Isabel Rodriguez, Singapore (SG); Chee Tiong Lim, Singapore (SG); Audrey Yoke Yee Ho, Crescent (SG)

(73) Assignees: ETHICON, INC., Somerville, NJ (US); AGENCY FOR SCIENCE TECHNOLOGY AND RESEARCH, Connexis (SG)

( * ) Notice: Subject to any disclaimer, the term of this patent is extended or adjusted under 35 U.S.C. 154(b) by 573 days.

(21) Appl. No.: 13/730,259

(22) Filed: Dec. 28, 2012

(65) Prior Publication Data
US 2013/0172927 A1 Jul. 4, 2013

Related U.S. Application Data

(60) Provisional application No. 61/581,545, filed on Dec. 29, 2011.

(51) Int. Cl.
*A61B 17/08* (2006.01)
*B29C 33/42* (2006.01)
(Continued)

(52) U.S. Cl.
CPC .......... *A61B 17/085* (2013.01); *A61F 2/0077* (2013.01); *B29C 33/424* (2013.01);
(Continued)

(58) Field of Classification Search
CPC ............ A61B 17/085; A61B 17/00234; A61B 2017/0495
(Continued)

(56) References Cited

U.S. PATENT DOCUMENTS 4,256,693 A 3/1981 Kondo et al.
4,464,254 A 8/1984 Dojki et al.
(Continued)

FOREIGN PATENT DOCUMENTS

CN 101849281 9/2010
DE 4126877 C1 11/1992
(Continued)

OTHER PUBLICATIONS

Anthony G. Gristina, "Biomaterial-Centered Infection: Microbial Adhesion Versus Tissue Integration", Science, vol. 237, pp. 1588-1595 (1987).
(Continued)

*Primary Examiner* — Victor Nguyen
(74) *Attorney, Agent, or Firm* — Roberts Mlotkowski Safran Cole & Calderon, P.C.

(57) ABSTRACT

An implant having an adhesive structure comprising a planar surface having two sides and rectangular cuboid-based protrusions having pyramidal tips extending from at least one of said sides, optionally having a porous basic supporting structure, and methods of making and using such implants.

31 Claims, 7 Drawing Sheets

(51) Int. Cl.
*B29C 59/02* (2006.01)
*A61B 17/00* (2006.01)
*A61F 2/00* (2006.01)
*A61B 17/04* (2006.01)
*B29L 31/00* (2006.01)

(52) U.S. Cl.
CPC ...... *B29C 59/022* (2013.01); *A61B 17/00234* (2013.01); *A61B 2017/00004* (2013.01); *A61B 2017/00526* (2013.01); *A61B 2017/0495* (2013.01); *A61F 2/0063* (2013.01); *A61F 2002/0081* (2013.01); *A61F 2230/0086* (2013.01); *B29C 2059/023* (2013.01); *B29K 2883/00* (2013.01); *B29K 2995/006* (2013.01); *B29K 2995/0056* (2013.01); *B29L 2031/756* (2013.01); *B29L 2031/7562* (2013.01)

(58) Field of Classification Search
USPC .................................................. 606/213, 215
See application file for complete search history.

(56) References Cited

U.S. PATENT DOCUMENTS

| | | | |
|---|---|---|---|
| 4,557,264 A | 12/1985 | Hinsch | |
| 4,753,776 A | 6/1988 | Hillman et al. | |
| 4,875,259 A | 10/1989 | Appledorn | |
| 4,911,165 A | 3/1990 | Lennard et al. | |
| 4,959,265 A | 9/1990 | Wood et al. | |
| 4,960,420 A | 10/1990 | Goble et al. | |
| 5,011,494 A | 4/1991 | von Recum et al. | |
| 5,176,692 A | 1/1993 | Wilk et al. | |
| 5,246,451 A | 9/1993 | Trescony et al. | |
| 5,246,666 A | 9/1993 | Vogler et al. | |
| 5,324,519 A | 6/1994 | Dunn et al. | |
| 5,344,611 A | 9/1994 | Volger et al. | |
| 5,352,229 A | 10/1994 | Marlowe | |
| 5,455,009 A | 10/1995 | Volger et al. | |
| 5,569,272 A | 10/1996 | Reed et al. | |
| 5,723,219 A | 3/1998 | Kolluri et al. | |
| 6,217,540 B1 | 4/2001 | Yazawa et al. | |
| 6,220,453 B1 | 4/2001 | Kitajima et al. | |
| 6,267,772 B1 | 7/2001 | Mulhauser et al. | |
| 6,368,871 B1 | 4/2002 | Christel et al. | |
| 6,403,655 B1 | 6/2002 | Bezwada et al. | |
| 6,485,503 B2 | 11/2002 | Jacobs et al. | |
| 6,638,284 B1 | 10/2003 | Rousseau et al. | |
| 6,703,041 B2 | 3/2004 | Burns et al. | |
| 6,720,469 B1 | 4/2004 | Curtis et al. | |
| 6,872,439 B2 | 3/2005 | Fearing et al. | |
| 6,913,697 B2 | 7/2005 | Lopez et al. | |
| 7,032,889 B1 * | 4/2006 | Moss ............... | E04H 17/00 256/11 |
| 7,074,294 B2 | 7/2006 | Dubrow | |
| 7,195,872 B2 | 3/2007 | Agrawal et al. | |
| 7,331,199 B2 | 2/2008 | Ory et al. | |
| 7,479,318 B2 | 1/2009 | Jagota et al. | |
| 7,745,223 B2 | 6/2010 | Schubert et al. | |
| 7,754,233 B2 | 7/2010 | Andjelic et al. | |
| 7,988,733 B2 | 8/2011 | Shimp et al. | |
| 3,016,741 A1 | 9/2011 | Weiser et al. | |
| 8,057,383 B2 | 11/2011 | Weiser et al. | |
| 8,133,484 B2 | 3/2012 | Preiss-Bloom et al. | |
| 8,307,831 B2 * | 11/2012 | Rousseau ............... | 128/848 |
| 8,944,989 B2 | 2/2015 | Weiser et al. | |
| 9,022,920 B2 | 5/2015 | Weiser et al. | |
| 2003/0074021 A1 | 4/2003 | Morriss et al. | |
| 2003/0208888 A1 | 11/2003 | Fearing et al. | |
| 2003/0220656 A1 * | 11/2003 | Gartstein ............... | A45D 26/0004 606/131 |
| 2004/0076822 A1 | 4/2004 | Jagota et al. | |
| 2004/0125266 A1 | 7/2004 | Miyauchi et al. | |
| 2004/0138705 A1 | 7/2004 | Heino et al. | |
| 2005/0065463 A1 | 3/2005 | Tobinaga et al. | |
| 2005/0095699 A1 | 5/2005 | Miyauchi et al. | |
| 2005/0106552 A1 | 5/2005 | Ikeda | |
| 2005/0181629 A1 | 8/2005 | Jagota et al. | |
| 2006/0034734 A1 | 2/2006 | Schubert et al. | |
| 2006/0078724 A1 | 4/2006 | Bhushan et al. | |
| 2006/0087053 A1 * | 4/2006 | O'Donnell et al. ......... | 264/156 |
| 2006/0005362 A1 | 6/2006 | Arzt et al. | |
| 2006/0154063 A1 | 7/2006 | Fujihara et al. | |
| 2006/0204738 A1 | 9/2006 | Dubrow et al. | |
| 2007/0191958 A1 * | 8/2007 | Abdou ............... | A61B 17/025 623/17.16 |
| 2007/0227967 A1 | 10/2007 | Sakaino et al. | |
| 2007/0299542 A1 | 12/2007 | Mathisen et al. | |
| 2008/0124246 A1 | 5/2008 | Diaz-Quijada et al. | |
| 2008/0217180 A1 | 9/2008 | Doye et al. | |
| 2008/0241512 A1 | 10/2008 | Boris et al. | |
| 2008/0241926 A1 | 10/2008 | Lee et al. | |
| 2008/0280085 A1 | 11/2008 | Livne | |
| 2009/0130372 A1 | 5/2009 | Fukui et al. | |
| 2000/9031843 | 12/2009 | Van Holten et al. | |
| 2009/0318843 A1 | 12/2009 | Van Holten et al. | |
| 2010/0098909 A1 | 4/2010 | Reyssat et al. | |
| 2010/0137903 A1 | 6/2010 | Lee et al. | |
| 2010/0249913 A1 | 9/2010 | Datta et al. | |
| 2011/0063610 A1 | 3/2011 | Ivanov et al. | |
| 2011/0021965 A1 | 6/2011 | Karp et al. | |
| 2011/0160869 A1 | 6/2011 | Duch et al. | |
| 2011/0172760 A1 | 7/2011 | Anderson | |
| 2011/0177288 A1 | 7/2011 | Bhushan et al. | |
| 2011/0178535 A1 * | 7/2011 | Whitman ............ | A61B 17/0057 606/139 |
| 2011/0282444 A1 | 11/2011 | Liu et al. | |
| 2011/0293667 A1 | 12/2011 | Baksh et al. | |
| 2012/0052234 A1 | 3/2012 | Natarajan et al. | |
| 2012/0143228 A1 | 7/2012 | Natarajan et al. | |
| 2012/0251611 A1 | 10/2012 | Luong-Van et al. | |
| 2012/0302427 A1 | 11/2012 | Elmouelhi et al. | |
| 2012/0302465 A1 | 11/2012 | Elmouelhi et al. | |
| 2013/0206330 A1 | 8/2013 | Natarajan et al. | |
| 2013/0266761 A1 | 10/2013 | Ho et al. | |
| 2013/0267880 A1 | 10/2013 | Luong-Van et al. | |
| 2013/0288225 A1 | 10/2013 | Elmouelhi et al. | |

FOREIGN PATENT DOCUMENTS

| | | |
|---|---|---|
| DE | 19832634 A1 | 1/2000 |
| EP | 0358372 A1 | 3/1990 |
| EP | 1416303 | 5/2004 |
| EP | 2062611 A1 | 5/2009 |
| JP | 02-088049 A | 3/1990 |
| JP | 02-298569 A | 12/1990 |
| JP | H02-298569 A | 12/1990 |
| JP | 06-327697 A | 11/1994 |
| JP | H06-327697 A | 11/1994 |
| JP | 2003-03533326 A | 11/2003 |
| JP | 2004170935 A | 6/2004 |
| JP | 2005-6852 A | 1/2005 |
| JP | 2006-515774 A | 6/2006 |
| JP | 2008-200793 A | 9/2008 |
| JP | 2011-235122 A | 11/2011 |
| JP | 2013-226413 A | 11/2013 |
| RU | 2173177 C1 | 9/2001 |
| RU | 2225705 C2 | 3/2004 |
| SG | 193370 A | 10/2013 |
| WO | 0056808 | 9/2000 |
| WO | 03/099160 A1 | 12/2003 |
| WO | 2004/094303 A2 | 11/2004 |
| WO | 2006031197 | 3/2006 |
| WO | 2009/123739 A1 | 4/2008 |
| WO | 2008/076390 A3 | 6/2008 |
| WO | 2008/102620 A1 | 8/2008 |
| WO | 2009022911 A2 | 2/2009 |
| WO | 2009029045 | 3/2009 |
| WO | 2009/067482 A1 | 5/2009 |
| WO | 2010033725 A2 | 3/2010 |
| WO | 2010/129641 A1 | 11/2010 |
| WO | 2011/026987 A1 | 3/2011 |
| WO | WO 2012/030570 A1 | 3/2012 |

(56) References Cited

FOREIGN PATENT DOCUMENTS

| WO | WO 2012/162452 A2 | 11/2012 |
|---|---|---|
| WO | WO 2013/102085 A1 | 7/2013 |
| WO | WO 2013/163304 A1 | 10/2013 |

OTHER PUBLICATIONS

Ji Yeong Won et al., "The Fabrication of Protein Nano Arrays Using 3-Dimensional Plastic Nanopillar Patterns", Nanoscience and Nanotechnology, vol. 11, pp. 4231-4235 (2011).
Ning Zhao et al., "Self-organized Polymer Aggregates with a Biomimetic Hierarchical Structure and its Superhydrophobic Effect", Cell Biochem Biophys, vol. 49, pp. 91-97 (2007).
Bharat Bhushan et al., "Self-Cleaning Efficiency of Artificial Superhydrophobic Surfaces" Langmuir, vol. 25, No. 5, pp. 3240-3248 (2009).
Jun Shi et al., "Towards Bioinspired Superhydrophobic Ply(L-lactiv acid) Surfaces Using Phase Inversion-Based Methods", Bioinspiration & Biomimetics, vol. 3, pp. 1-6 (2008).
Yong Chae Jung et al., "Wetting Behavior of Water and Oil Droplets in Three-Phase Interfaces for Hydrophobicity/philicity and Oleophobicity/philicity", Langmuir, vol. 25 (24), pp. 14165-14173 (2009).
Yuwon Lee et al., "Fabrication of Hierarchical Structures on a Polymer Surface to Mimic Natural Superhydrophobic Surfaces", Advanced Materials, vol. 19, pp. 2330-2335 (2007).
Kyoung Je Cha et al., "Effect of Replicated Polymeric Substrate with Lotus Surface Structure on Adipose-Derived Stem Cell Behaviors", Macromoleculare Bioscience, vol. 11, pp. 1357-1363 (2011).
Takashi Yanagishita et al., "Anti-Reflection Structures on Lenses by Nanoimprinting Using Ordered Anodic Porous Alumina", Applied Physics Express 2, pp. 022001-1-022001-3 (2009).
Anna J. Schulte et al., "Hierarchically Structured Superhydrophobic Flowers with Low Hysteresis of the Wild Pansy (Viola Tricolor)—New Design Principles for Biomimetic Materials", Beilstein J. Nanotechnol, vol. 2, pp. 228-236 (2011).
Bharat Bhushan et al., "Micro-, Nano- and Hierarchical Structures for Superhydrophobicity, Self-Cleaning and Low Adhesion", Philosophical Transaction of the Royal Society, A (2009) 367, pp. 1631-1672. Downloaded from rsta.royalsocietypublishing.org on Mar. 2, 2012.
Sitti M. et al., High aspect ratio polymer micro/nano-structure manufacturing using nanoembossing, nanomolding and directed self-assembly; IEEE/ASME Advanced Mechatronics Conference, Kobe, Japan, Jul. 2003.
Tsougeni K. et al., Nano-texturing of poly(methyl methacrylate) polymer using plasma processes and applications in wetting control and protein adsorption; Journal Microelectronic Engineering, vol. 86 (2009) 1424-1427.
Vlachopoulou M.-E. et al., Effect of surface nanostructuring of PDMS on wetting properties, hydrophobic recovery and protein adsorption, Microelectronic Engineering,vol. 86, (2009) 1321-1324.
Occhiello, et al., "Oxygen-Plasma-Treated Polypropylene Interfaces with Air, Water, and Epoxy Resins: Part 1. Air and Water.", 1991, Journal of Applied Polymer Science, 42, pp. 551-559.
Gerard, et al., "Surface modification of polypropylene membranes used for blood filtration", 2011, Polymer, 52, pp. 1223-1233.
International Search report for International Application No. PCT/US2011/048584 dated Feb. 20, 2012.
International Search report for International Application No. PCT/US2012/072081 dated Mar. 12, 2013.
Sriram Natarajan, U.S. Appl. No. 12/871,745, filed Aug. 30, 2010.
Noha Elmouelhi, U.S. Appl. No. 13/116,721, filed May 26, 2011.
Sriram Natarajan, PCT No. PCT/US2011/048584 Filed Aug. 22, 2011.
Sriram Natarajan, U.S. Appl. No. 13/340,331, filed Dec. 29, 2011.
Noha Elmouelhi, U.S. Appl. No. 13/340,405, filed Dec. 29, 2011.
Emma Kim Luong-Van, U.S. Appl. No. 13/435,544, filed Mar. 30, 2012.
Audrey Yoke Yee Ho, U.S. Appl. No. 13/441,496, filed Apr. 6, 2012.
Emma Kim Luong-Van, U.S. Appl. No. 13/441,539, filed Apr. 6, 2012.
Noha Elmouelhi, U.S. Appl. No. 13/458,825, filed Apr. 27, 2012.
Noha Elmouelhi, PCT No. PCT/US2012/039256 filed May 12, 2012.
Sriram Natarajan, PCT No. PCT/US2012/072081 filed Dec. 28, 2012.
Sriram Natarajan, U.S. Appl. No. 13/841,561, filed Mar. 15, 2013.
Noha Elmouelhi, PCT No. PCT/US2013/038007 filed Apr. 24, 2013.
Audrey Yoke Yee Ho, U.S. Appl. No. 14/139,673, filed Dec. 23, 2013.
Roure, et al., "Force Mapping in Epithelial Cell Migration", pp. 2390-2395, PNAS, Feb. 15, 2005, vol. 102, No. 7.
Oxford Dictionary Online Definition of "Cylinder".
International Search Report for PCT/US2012/039256 dated Mar. 5, 2013.
Wan Y., et al., "Characterization of surface property of poly (lactide-co-glycolide) after oxygen plasma treatment", Biomaterials, Elsevier Science Publishers, vol. 25, No. 19, Aug. 1, 2004, pp. 4777-4783.
Jianhua Wei, et al., "Influence of surface wettability on competitive protein adsorption and initial attachment of osteoblasts; Competitive protein adsorption and initial cell attachment", Biomedical Materials, Institute of Physics Publishing, vol. 4, No. 4, Aug. 1, 2009, p. 45002.
Tsougeni K., et al., "Mechanisms of oxygen plasma nanotexturing of organic polymer surfaces: From stable super hydrophilic to super hydrophobic surfaces", Langmuir, American Chemical Society, vol. 25, No. 19, Oct. 6, 2009, pp. 11748-11759.
Messina G.M.L., et al., "A multitechnique study of preferential protein adsorption on hydrophobic and hydrophilic plasma-modified polymer surfaces", Colloids and Surfaces. B., Biointerfaces, vol. 70, No. 1, Apr. 1, 2009, pp. 76-83.
Chen H. et al., "The effect of surface microtopography of poly (dimethylsiloxane) on protein adsorption, platelet and cell adhesion", Colloids and Surfaces. B., Biointerfaces, vol. 71, No. 2, Jul. 1, 2009, pp. 275-281.
Definition of "Integral", Merriam-Webster Dictionary online, pp. 1-3, Accessed Oct. 15, 2013.
S.D. Lee, "Surface Modification of Polypropylene Under Argon and Oxygen-RF-Plasma Conditions", Plasmas and Polymers, vol. 2, No. 3, Sep. 1, 1997, pp. 177-198.
International Search Report for PCT/US2013/038007 dated Jun. 18, 2013.
Saez et al., "Rigidity-driven growth and migration of epithelial cells on microstructured anisotropic substrates", PNAS, vol. 104, No. 20, pp. 8281-8286, May 15, 2007.
Search Report of Singapore Patent Application No. 2013086434 dated Dec. 4, 2014.
Written Opinion of Singapore Patent Application No. 2013086434 dated Jan. 16, 2015.
Chang, T.C., Plasma Surface Treatment in Composites Manufacturing, Journal of Industrial Technology, Nov. 1, 1998-Jan. 1999, vol. 15, No. 1, pp. 1-7, Table 1.
Office Action dated May 22, 2015 in U.S. Appl. No. 13/116,721; 27 pages.
Office Action dated May 22, 2015 in U.S. Appl. No. 13/340,405; 30 pages.
Notice of Allowance dated Aug. 6, 2015 in U.S. Appl. No. 13/841,561; 4 pages.
European Search Report EP12863230 dated Jul. 10, 2015.
Gomathi, N. and Neogi, S., J Adhes Sci Technol, 2009, vol. 23, p. 1811-26.
Tyan, Y.C. et al., Chinese Journal of Medical and Biological Engineering, 2000, vol. 20, No. 1, p. 25-30.
Liao, J.D. et al., Biomacromolecules, 2005, vol. 6, p. 392-9.
A. Shekaran et al. "Extracellular matrix-mimetic adhesive biomaterials for bone repair", Journal of Biomedical Materials Research, Part A, Jan. 2011, pp. 261-272, vol. 96 No. 1, Wiley Periodicals, Inc.

(56) References Cited

OTHER PUBLICATIONS

D S Abakarova et al. "Two-layer adhesive film Diplen-denta C—a new compound containing polymer base and active component Solcoseryl", Stomatologiia, Feb. 2007, vol. 86, No. 1, pg. 70-71, English Abstract Only.
International Preliminary Report on Patentability issued in International Application No. PCT/US2012/072081 dated Jul. 1, 2014.
International Preliminary Report on Patentability issued in International Application No. PCT/US2011/048584 dated Mar. 5, 2013.
International Preliminary Report on Patentability issued in International Application No. PCT/US2012/039256 dated Nov. 26, 2013.
International Preliminary Report on Patentability issued in International Application No. PCT/US2013/038007 dated Oct. 28, 2014.

* cited by examiner ered-to substrate, e.g., living tissue, an implant that provides adhesion by non-chemical interactions

ADHESIVE STRUCTURE WITH TISSUE PIERCING PROTRUSIONS ON ITS SURFACE

RELATED APPLICATION

This application claims the benefit of Provisional Application Ser. No. 61/581,545, filed on Dec. 29, 2011, the contents of which are hereby incorporated by reference in their entirety.

FIELD OF THE INVENTION

The present invention relates to polymer-based structures having shapes and mechanical properties that optimize adhesion to a specific target, e.g., a tissue or organ target.

BACKGROUND OF THE INVENTION

There is an ongoing need for medical implants having improved adhesion. Such implants can be suited to use in various applications such as an adjunct to or replacement for sutures and staples used to close surgical incisions.

Tissue reinforcing implants, commonly referred to as areal implants or meshes, have been developed that match or compliment the mechanical properties of the underlying tissue. These implants generally require the use of sutures or staples around the entire periphery of the implant to hold the implant in the surgical site. It would be highly desirable to have an implant that can be placed on the surgical site and maintains its placement without using sutures or staples.

U.S. Pat. No. 7,331,199 to Ory et al. discloses a prosthetic knit for medical or surgical use which has a structure made of monofilament and/or multifilament yarn which is biocompatible and optionally partially bioabsorbable. According to the invention, this knit comprises a monofilament sheet forming, on one face of the knit, spiked naps which protrude perpendicularly with respect to said sheet, that is to say naps each having a substantially rectilinear body and, at the free end of this body, a head of greater width than that of this body.

U.S. Pat. No. 6,485,503 to Jacobs et al. discloses a tissue approximation device and processes for using the device. The device is an implantable, biodegradable construct (except for hernia repairs) that has attachment points emanating from a supportive backing. The device improves the mechanical phase of wound healing and evenly distributes tension over the contact area between the device and tissue. Processes for using the device include wound closure, vascular anastomoses, soft tissue attachment and soft tissue to bone attachment. Several variations are particularly applicable to facilitating tissue approximation in surgical cosmetic applications, particularly brow lifts. Generally, scalp tissue to be lifted may be set on a brow lift device via attachment points, and the device may then be secured to a patient's cranium. Variations of the device are described along with a method of installing the brow lift device. Also described is a tool particularly useful for installing a brow lift device.

World Patent No. WO 2009/067482 to Karp et al. discloses an adhesive article including a biocompatible and at least partially biodegradable substrate having a surface; and a plurality of protrusions extending from the surface. The protrusions include a biocompatible and at least partially biodegradable material, and have an average height of less than approximately 1,000 micrometers.

For the adhered-to substrate, e.g., living tissue, an implant that provides adhesion by non-chemical interactions between the implant and the substrate would be highly desirable. Additionally, it would be highly desirable to provide an implant with adhesive structures that would limit damage to the tissue it contacted by being optimized to pierce and attach to the tissue but small enough not to damage the tissue.

SUMMARY OF THE INVENTION

In a first embodiment, the invention is directed to an adhesive structure comprising a planar surface having two sides and rectangular cuboid-based protrusions having pyramidal tips extending from at least one of said sides.

In another embodiment, the invention is directed to a process for making an adhesive structure, comprising providing a mold having multiple rectangular cuboid-based indentations having pyramidal tips extending below a planar surface, applying a melt processable polymer to said mold so as to fill said indentations and said planar surface to form a first molded adhesive structure having a planar surface and rectangular cuboid-based protrusions having pyramidal tips extending below said planar surface, and removing said molded adhesive structure from said mold.

Another embodiment of the present invention is directed to a surgical procedure comprising inserting into a patient at a surgical repair site an implant comprising an adhesive structure comprising a planar surface having two sides and rectangular cuboid-based protrusions having pyramidal tips extending from at least one of said sides; approximating edges of the surgical repair site; and pressing said adhesive structure against the surgical repair site.

Another embodiment of the present invention is directed to a surgical procedure comprising inserting into a patient at a surgical repair site an implant comprising an adhesive structure comprising a planar surface having two sides and rectangular cuboid-based protrusions having pyramidal tips extending from at least one of said sides; approximating edges of the surgical repair site; and pressing said adhesive structure against the surgical repair site substantially without mechanical fixation of the device.

Another embodiment of the present invention is directed to a process for making an adhesive structure, comprising providing a mold having multiple rectangular cuboid-based indentations having pyramidal tips extending below a planar surface; applying a melt processable polymer film to said planar surface; applying a porous basic structure onto said polymer film; applying a sufficient pressure and temperature to said porous basic structure and said polymer film to force a portion of said film into said indentations and to simultaneously laminate said porous basic structure to said film; and removing said molded adhesive structure from said mold.

Another embodiment of the present invention is directed to an adhesive structure comprising a perforated planar surface having two sides and protrusions extending from at least one of said sides.

DETAILED DESCRIPTION

The present invention is directed to an adhesive structure for an implant that provides adhesion by mechanical, non-chemical interactions between the implant and a target tissue, and which limits damage to the target tissue by having adhesive protrusions optimized to pierce and attach to the target tissue, but small enough not to damage the tissue.

For purposes of the present invention, a target substrate can include biological target tissue, or non-tissue, e.g., a surface associated with a medical device. In certain embodiments, the target substrate can be associated with the adhesive structure itself, e.g., in the case of a substrate or film comprising protrusions on either side, which can be utilized as a double-sided adhesive tape. Such double-sided embodiments can even be wrapped around itself or similar adhesive structures.

Figure 1:
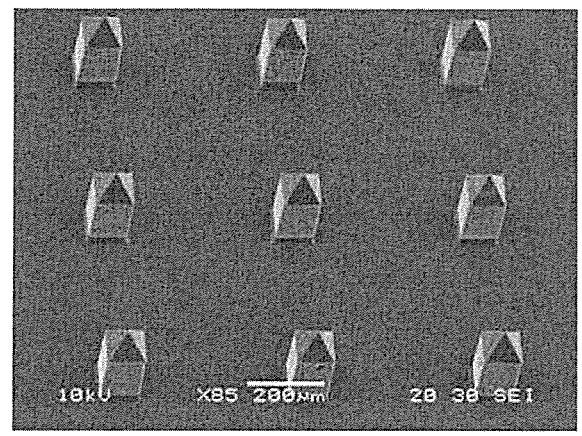
FIG. 1 depicts a scanning electron microscope image of an adhesive structure according to the present invention which is a polypropylene substrate having straight wall protrusions.

The present invention relates to polymer-based adhesive micro/nano structures with formed surface features and mechanical properties that optimize adhesion to a specific target tissue. The structures contain pillar-like tissue piercing protrusions extending from the surface thereof (FIGS. 1, 2A and 2B), which can be of a specific width, length, aspect ratio (height/width), and spacing, which can be fabricated with various polymers, such as melt processable polymers. The sizes and shapes of the protrusions can be selected to enhance adhesion to specific target substrates, e.g., various tissue types. Suitable polymers for use in the present invention include polymers that can be hydrophilic or hydrophobic, or bio-absorbable or non bio-absorbable (i.e. biodurable), depending on their intended use and target substrate.

Figures 2A, 2B:
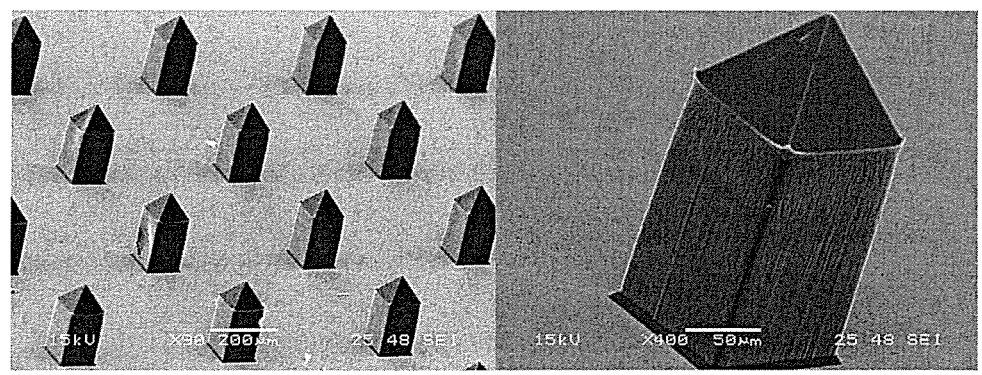
FIGS. 2A and 2B depict scanning electron microscope images of adhesive structures according to the present invention, which is a polydioxanone substrate with straight wall protrusions.

In one aspect, the present invention relates to an adhesive structure comprising a planar substrate with a surface from which extend tissue piercing protrusions, e.g., substantially squared-based protrusions, such as rectangular cuboid-based protrusions, having substantially pyramidal tips extending therefrom, as shown in FIG. 2B. The protrusions promote adhesion without chemical interaction, but instead by mechanically interacting with a target tissue by piercing said tissue in multiple places with the protrusions so as to increase adhesion between the adhesive structure and a target surface to which the adhesive structure is to be adhered, as measured by shear adhesion.

Figures 3A, 3B:
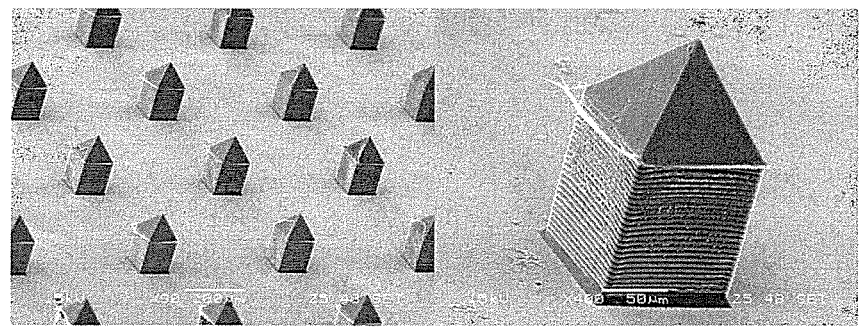
FIGS. 3A and 3B depict scanning electron microscope images adhesive structures according to the present invention, which is a polydioxanone substrate with serrated wall protrusions.
Figures 4A, 4B:
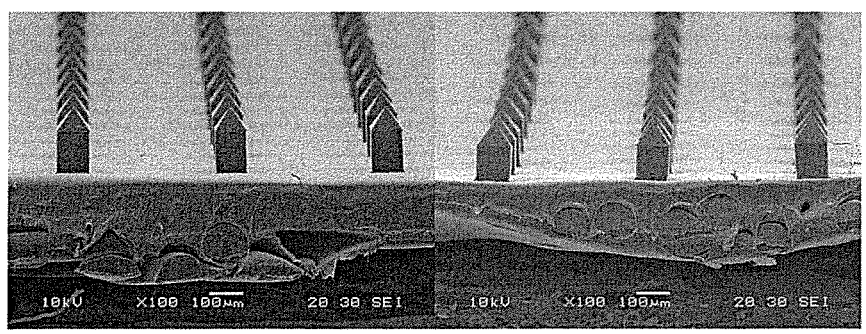
FIGS. 4A and 4B depict scanning electron microscope images of an adhesive structure according to the present invention which is a polypropylene mesh laminate with polyglecaprone 25 protrusions.

According to the present invention, the substantially pyramidal tips of the tissue piercing protrusions can be defined as square pyramids, i.e. a pyramidal structure having four triangular sides of equal area, and a square base of the same area as the upper or terminal end of the substantially squared-based protrusions. In an advantageous embodiment, the faces of the tissue piercing protrusions are serrated, such as illustrated in FIGS. 3A and 3B.

In another aspect, the present invention relates to a polymer-containing adhesive structure comprising a substrate having an adhesive surface which includes tissue piercing protrusions, e.g., substantially squared-based protrusions with substantially pyramidal tips, of sufficient height, width, aspect ratio and spacing for the surface to interact with the target surface to promote adhesion, as measured by shear adhesion. For present purposes, structures include sub-millimeter, micron-dimensioned and sub-micron-dimensioned structures, e.g., nano-dimensioned structures, whose lengths (or heights) typically exceed their widths. In another embodiment, the tissue piercing protrusions with substantially squared-based protrusions with substantially pyramidal tips where the square-bases' width at its proximal and distal ends are essentially the same and the pyramidal tip's included angle is essentially 54 degrees.

Advantageously, the protrusions extend substantially normal to the planar surface, such as at an angle within about +/−10 degrees of normal, preferably within about +/−5 degrees of normal to the planar surface. The protrusions can have aspect ratios, measured as the ratio of height/width, of at least about 0.5, advantageously from at least about 1 to about 5.

The adhesive structure has protrusions which are in the shape of rectangular cuboid bases, having widths from about 1 to 500 microns, or between about 50 and 250 microns, or from about 50 to 100 microns, or even from about 10 to 50 microns, and the protrusions have heights greater than or equal to about 0.5 micron. The spacing between the protrusions can be varied, such as between about 1 to 500 microns, or even between about 50 to 250 microns. The dimensions can be tailored to match corresponding dimensions of the target tissue, such that maximum adhesion can be obtained.

The adhesive structure can have a protrusion density of from about 400 to about 20,000 protrusions/cm$^2$, such as from about 3500 to about 15,000 protrusions/cm$^2$. For present purposes, "protrusion density" can be described as the number of protrusions or pillars present per square centimeter of adhesive structure surface.

In a non-limiting example, the adhesive structure of the present invention can be a biocompatible polymeric film having a planar surface, wherein the protrusions are integral with said film surface and extend therefrom. The polymer of said biocompatible polymeric film and protrusions can a biodurable polymer, i.e. one that does not resorb in vivo, or a bioabsorbable polymer, i.e. one that does resorb in vivo, and is preferably a bioabsorbable polymer.

A bioabsorbable polymer is one capable of being decomposed by the action of biological agents, e.g., bacteria, enzymes or water. Suitable bioabsorbable polymers useful as films in the present invention include, but are not limited to, aliphatic polyesters, poly (amino acids), copoly (ether-esters), polyalkylene oxalates, tyrosine-derived polycarbonates, poly (iminocarbonates), polyorthoesters, polyoxaesters, polyamidoesters, polyoxaesters containing amine groups, poly(anhydrides), polyphosphazenes, collagen, elastin, hyaluronic acid, laminin, gelatin, keratin, chondroitin sulfate, polyglycolide (PGA), poly(propylenefumarate), poly(cyanoacrylate), polycaprolactone (PCL), poly(trimethylene carbonate), poly(lactide), poly(dioxanone), poly(glycerol sebacate) (PGS), poly(glycerol sebacate acrylate) (PGSA), and biodegradable polyurethanes.

Suitable biodurable materials for use as films in the present invention include, but are not limited to polyamides (polyhexamethylene adipamide (nylon-6,6), polyhexamethylene sebacamide (nylon-6,10), polycapramide (nylon-6), polydodecanamide (nylon-12) and polyhexamethylene isophthalamide (nylon-6,1) copolymers and blends thereof, polyesters (e.g. polyethylene terephthalate, polybutyl terephthalate, copolymers and blends thereof), fluoropolymers (e.g. polytetrafluoroethylene copolymers and polyvinylidene fluoride), polyolefins (e.g. polypropylene including isotactic and syndiotactic polypropylene and blends thereof, as well as, blends composed predominately of isotactic or syndiotactic polypropylene blended with heterotactic polypropylene, such as are described in U.S. Pat. No. 4,557,264 issued Dec. 10, 1985 assigned to Ethicon, Inc. hereby incorporated by reference, and polyethylene, such as is described in U.S. Pat. No. 4,557,264 issued Dec. 10, 1985 assigned to Ethicon, Inc. hereby incorporated by reference, and combinations thereof.

In a particularly preferred embodiment, to be discussed in detail below, the film polymers are suitably elastomeric polymers, including but not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70); elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and epsilon-caprolactone. In another embodiment, the elastomeric copolymer is a copolymer of lactide and epsilon-caprolactone.

In still another aspect, the present invention relates to an adhesive structure comprising a two-sided substrate, from each side of which extend the tissue piercing protrusions described above; i.e., wherein said protrusions extend from both sides of the planar surface of the adhesive structure. Such two-sided adhesive structures can be advantageous for use as for example, a double-sided adhesive tape, which can even be wrapped around itself or similar adhesive structures. In such case, the protrusions from one side can temporarily adhere to the protrusions on the other side, so as to maintain for example a tubular shape which can be inserted through a trocar or the like.

In a particularly preferred embodiment, the present invention is directed to an adhesive structure as described above, further comprising a porous basic structure, such as a surgical mesh attached to the side of said planar surface opposite said protrusions. The porous basic structure is provided to reinforce the adhesive structure, and is preferably comprised of a biodurable polymer.

The porous basic structure to which the adhesive structure is laminated can be a surgical mesh as described in U.S. Pat. No. 6,638,284, incorporated by reference herein in its entirety. It is desirable for a surgical mesh fabric to exhibit certain properties and characteristics. In particular, the mesh should have a burst strength sufficient to ensure that the mesh does not break or tear after insertion into a patient. The mesh should also have a pore size that enables easy visualization of structures through the mesh, minimize camera light reflection and provide a density of crossing fibers sufficient to facilitate fastening in an endoscopic environment. In addition, the construction of the mesh should provide the maximum burst resistance while minimizing foreign body mass and enhancing fabric pliability.

The surgical mesh is preferably fabricated from a yarn that is biocompatible. Preferred are yarns that have already been accepted for use as a suture material. Numerous biocompatible absorbable (bioabsorbable) and non-absorbable (biodurable) yarns can be used to make the surgical meshes described hereinafter.

Suitable biodurable materials for use in the present invention include, but are not limited to, cotton, linen, silk, polyamides (polyhexamethylene adipamide (nylon-6,6), polyhexamethylene sebacamide (nylon-6,10), polycapramide (nylon-6), polydodecanamide (nylon-12) and polyhexamethylene isophthalamide (nylon-6,1) copolymers and blends thereof, polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene, such as are described in U.S. Pat. No. 4,557,264 issued Dec. 10, 1985 assigned to Ethicon, Inc. hereby incorporated by reference, and polyethylene, such as is described in U.S. Pat. No. 4,557,264 issued Dec. 10, 1985 assigned to Ethicon, Inc. hereby incorporated by reference, and combinations thereof.

Such biodurable polymers also include, but are not limited to, acrylics, polyamide-imide (PAI), polyetherketones (PEEK), polycarbonate, polyethylenes (PE), polybutylene terephthalates (PBT), polyethylene terephthalates (PET), polypropylene, polyamide (PA), polyvinylidene fluoride (PVDF), and polyvinylidene fluoride-co-hexafluoropropylene (PVDF/HFP), polymethyl-methacrylate (PMMA), polyvinylalcohol (PVA), polyhydroxyethylmethacrylate, polyvinylalcohol (PVA), polyhydroxyethylmethacrylate (PHEMA), poly(N-isopropylacrylamide) (PNIPAAm), expanded polytetrafluoroethylene (EP-PTFE), and other polyolefins.

The preferred polypropylene yarns for the present invention utilizes as the raw material pellets of isotactic polypropylene homopolymer having a weight average molecular weight of from about 260,000 to about 420,000. Polypropylene of the desired grade is commercially available in both powder and pellet form.

Suitable bioabsorbable (or biodegradable) materials for use as yarns include, but are not limited to aliphatic polyesters which include but are not limited to homopolymers and copolymers of lactide (which includes lactic acid d-,l- and meso-lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one and polymer blends thereof.

Fibers and/or yarns may be made from bioabsorbable and biodurable materials described above in heterologous yarns or bicomponent yarns. Additionally, fibers with different materials used in the sheath and core may also be used for the surgical meshes.

In a preferred embodiment, the surgical mesh is fabricated from a monofilament yarn formed from a polypropylene resin, such as that disclosed in U.S. Pat. No. 4,911,165, entitled "Pliablized Polypropylene Surgical Filaments" and assigned to Ethicon, Inc., the contents of which is hereby incorporated in its entirety by reference. The preferred monofilament polypropylene yarn used has a diameter of from about 3.0 to about 6.0 mils, and more preferably a diameter of about 3.5 mils. Alternatively, a multifilament yarn, such as a multifilament polypropylene yarn may be used to fabricate a surgical mesh in accordance with the present invention.

The porous basic structure can be one having pores extending between the first and second major surfaces thereof. In one embodiment, the porous basic structure preferably includes an isotropic material, or an anisotropic material adapted to have more stretch along a first axis and less stretch along a second axis that traverses the first axis. In certain embodiments, the porous basic structure according to the invention has a mesh-like basic structure with pores, the size of which over more than 90% of the total area of the pores lies in the range from 1.5 mm to 8 mm. Due to the relatively large pores, the pores preferably account for at least 50% of the basic area of the mesh-like basic structure.

The porous basic structure is typically areal in form, e.g. as a woven fabric, or a knitted fabric, or a nonwoven fabric or even a porous film, such as an expanded PTFE film. The term "knitted fabric" is to be understood here in the widest sense. It also includes, for example, knits and other mesh structures, i.e. essentially all textile materials which are not strictly woven fabrics. The basic structure is preferably weft-knitted or warp-knitted.

The knitted fabric of the porous basic structure preferably has an approximate rectangular structure or approximate quadratic structure knitted from yarns. Honeycomb structures or structures with approximately circular openings or other polygonal structures are also conceivable. In one aspect, the adhesive structure can have a generally oval shape. It is contemplated that the particular areal shape of the adhesive structure may be modified and still fall within the scope of the present invention. In other embodiments, the implant may have a circular, square, or rectangular shape.

A great many configurations are in general conceivable for the porous basic structure, for example areal structures, mesh-like structures, knitted mesh-like structures, supports for tissue cultures, supports for cell cultures, supports for active substances, textile configurations, and three-dimensional structures.

The porous basic structure can contain, in addition to a biodurable polymer, a bioabsorbable polymer, preferably containing monofilaments and/or multifilaments. The filaments of are preferably monofilaments with a thickness in the range of from 0.04 mm to 0.5 mm. In addition, mixed forms are conceivable, including forms such as yarns, monofilaments, multifilaments or twines, the thickness being preferably in the range of from 0.01 mm to 0.5 mm, while the width, in the case of a tape, is preferably in the range of from 0.05 mm to 1 mm.

In a preferred embodiment, the porous basic structure is composed of a biodurable polymer and the adhesive structure of a bioabsorbable polymer. Particularly preferred materials for the porous basic structure are polypropylene and mixtures of polyvinylidene fluoride and copolymers of vinylidene fluoride and hexafluoropropene, but other materials are also conceivable. In another embodiment, the material comprises combinations of copolymers of glycolide and caprolactone, poly-p-dioxanone and polypropylene.

In a particularly advantageous embodiment, the supported adhesive structure, having the porous basic structure laminated thereto, further comprises an adhesion barrier on the side of the porous basic structure opposite the adhesive structure. Adhesion barriers are designed to inhibit post surgical adhesions from forming between adjacent tissues and/or organs, while the patient is recovering and healing from the surgery, and while new tissue is forming within the pores of the porous basic structure.

Suitable adhesion barriers for use with the present invention include, but are not limited to oxidized regenerated cellulose (e.g., INTERCEED absorbable adhesion barrier), polymeric films (e.g., MONOCRYL material), SupraSeal, adhesion barriers consisting of D,L-polylactide (PDLA-Copolymer), SurgiWrap (MAST Biosurgery, San Diego, Calif.) Adhesion Barrier Film made of polylactide (PLA), polyoxaesters (U.S. Pat. No. 6,403,655—incorporated by reference herein in its entirety), PEDG (U.S. Pat. No. 7,754,233, incorporated by reference herein in its entirety), enteric carrier materials (U.S. Patent Publication No. 2009/0318843, incorporated by reference herein in its entirety), hydrogel films or coatings that are biocompatible (e.g., ETHICON INTERCOAT™ Absorbable Adhesion Barrier Gel, SprayGel® Adhesion Barrier (Confluent Surgical, Waltham, Mass.) and Adhibit™ adhesion prevention gel (Angiotech Pharmaceuticals Inc., Vancouver, BC)—both polyethylene glycol-based precursor liquids, which rapidly cross-link on the target tissue to form a flexible, adherent, bioabsorbable gel barrier); Oxiplex®, Oxiplex®/SP and MediShield™ (flowable gel made of carboxymethylcellulose and polyethylene oxide), CoSeal Adhesion Prevention Products (polyethylene glycol polymer), Teflon PTFE materials (e.g., Gor-tex Surgical Membrane (W.L. Gore & Associates, Inc., Flagstaff, Ariz.), sodium hyaluronate based materials (e.g., ACP gel (Baxter, Italy); SEPRAFILM adhesion barrier from Genzyme (modified hyaluronic acid and carboxymethylcellulose—forms a hydrophilic gel); INTERGEL adhesion prevention solution, and biologics such as fibrinolytic agents (e.g., recombinant human tissue plasminogen activator (rt-PA)) and fibrin glues.

In another embodiment, the invention is directed to an adhesive structure further comprising a second planar surface having two sides with rectangular cuboid-based protrusions having pyramidal tips extending therefrom, laminated to said porous basic structure such that said protrusions extend from both sides of said structure. Accordingly, the two-sided substrate is selected from a single layer substrate, a double layer substrate comprising two skin layers, and a triple layer substrate having a core layer and two skin layers. Such two-sided adhesive structures can be useful in holding adjacent tissues together, when necessary.

In one embodiment, the adhesive structure preferably includes at least two bioabsorbable, transparent films each having a thickness of approximately in the range from about 10 Angstroms to about 300 um, in particular between about 10 Angstroms to about 200 um, even between about 20 μm to about 200 μm. The two bioabsorbable transparent films are preferably laminated to the respective major faces of the porous basic structure.

In another aspect, the implant may include an adhesive film, such as a film made from polydioxanone (e.g. PDS film), optionally provided with an alignment marker visible through said bioabsorbable transparent films, disposed between the second absorbable film and the second major surface of the tissue reinforcing film for laminating the first and second absorbable films to the porous basic structure. In one example, an anisotropic, porous basic structure includes a polymeric mesh, and the first and second absorbable films include a MONOCRYL (polyglecaprone 25) film.

The alignment marker can be in the form of color markings (for example in the form of stripes), for example with the aid of filaments of different color worked into the basic structure or with marking stripes imprinted onto the porous basic structure, or even on the PDS adhesive film, making handling of the implant easier, depending on the application.

In another aspect, the adhesive structure of the present invention can further comprise reactive chemical groups that interact with the target substrate. The chemical groups can be selected from pressure sensitive adhesives such as acrylates, adhesives applied in the molten state (hot melt adhesives), solvent based adhesives such as poly(vinyl acetate), multi-part adhesives that can be cured by radiation, heat or moisture such as cyanoacrylates, and urethanes, natural sealants such as fibrin sealants and starches, hydroxysuccinimides, and aldehydes. The chemical groups can be provided on at least a portion of the adhesive structure surface and capable of interacting with the target substrate.

In one embodiment, the adhesive structure may further include an active agent such as an antimicrobial agent. In one embodiment, the adhesive structure may include at least one biologically active agent that is preferably released locally after implantation. The biologically active agent may be applied to at least one of the layers of the composite adhesive structure, or just to the surgical mesh prior to combination with the adhesive structure(s).

Substances which are suitable as active agents may be naturally occurring or synthetic and may include but are not limited to, antibiotics, antimicrobials, antibacterials, antiseptics, chemotherapeutics, cytostatics, metastasis inhibitors, antideabetics, antimycotics, gynaecological agents, urological agents, anti-allergic agents, sexual hormones, sexual hormone inhibitors, haemostyptics, hormones, peptide-hormones, antidepressants, vitamins such as Vitamin C, antihistamines, naked DNA, plasmid DNA, cationic DNA complexes, RNA, cell constituents, vaccines, cells occurring naturally in the body or genetically modified cells. The active agents may be present in an encapsulated form or in an absorbed form. More specifically, in one embodiment, the surgical mesh, the first bioabsorbable film and/or the second bioabsorbable film may be impregnated with a liquid based therapeutic agent such as Gentamicin, Octenidine, Polyhexamethylene Biguanide (PHMB).

In one embodiment, the active agents may be antibiotics including such agents as gentamicin or ZEVTERA™ (ceftobiprole medocaril) brand antibiotic (available from Basilea Pharmaceutica Ltd., Basel Switzerland). In one embodiment, the adhesive structure may include broad band antimicrobials used against different bacteria and yeast (even in the presence of bodily liquids) such as octenidine, octenidine dihydrochloride (available as active ingredient Octenisept® disinfectant from Schulke & Mayr, Norderstedt, Germany as), polyhexamethylene biguanide (PHMB) (available as active ingredient in Lavasept® from Braun, Switzerland), triclosan, copper (Cu), silver (Ag), nanosilver, gold (Au), selenium (Se), gallium (Ga), taurolidine, N-chlorotaurine, alcohol based antiseptics such as Listerine® mouthwash, N a-lauryl-L-arginine ethyl ester (LAE), myristamidopropyl dimethylamine (MAPD, available as an active ingredient in SCHERCODINE™ M), oleamidopropyl dimethylamine (OAPD, available as an active ingredient in SCHERCODINE™ O), and stearamidopropyl dimethylamine (SAPD, available as an active ingredient in SCHERCODINE™ S). In one embodiment, the agent may be octenidine dihydrochloride (hereinafter referred to as octenidine) and/or PHMB. The active agents may be applied together with a bioabsorbable coating polymer to adjust the release time of the agents.

In another embodiment, the invention is directed to a method that can form adhesive structures having tissue-piercing protrusions extending from a generally planar surface, of sizes generally below about 500 microns or even of sub-micron sizes, which are large enough to penetrate a target tissue, but small enough to minimize tissue damage.

The adhesive structures of the current invention can be formed by providing a mold having multiple rectangular cuboid-based indentations having pyramidal tips extending below a planar surface; applying a melt processable polymer to said mold so as to fill said indentations and said planar surface to form a first molded adhesive structure having a planar surface and rectangular cuboid-based protrusions having pyramidal tips extending below said planar surface; and removing said molded adhesive structure from said mold.

The process can further comprise making a second molded adhesive structure substantially identical to said first molded adhesive structure, and laminating said first adhesive structure to said second adhesive structure, prior to removing said laminated structures from their respective molds. Additionally or alternatively, the process can further comprise laminating a porous basic structure, such as a surgical mesh, to said planar surface opposite said indentations, prior to withdrawing the first molded adhesive structure from said mold, so as to form a reinforced mesh/film adhesive structure.

The process can further comprise making a second molded adhesive structure, and laminating said second molded adhesive structure to said porous basic structure opposite said first molded adhesive structure, prior to removing said molded adhesive structures from their respective molds, to make, e.g. a film/mesh/film adhesive structure, as described above, having protrusions on both faces thereof.

The process includes the use of molds made by nanomolding means such as lithography, that lead to fabrication of the square-based, pyramidal tip adhesive structures, described above. In one embodiment, a silicon mold having an array of pillar-shaped depressions having rectangular cuboid-based protrusions with pyramidal tips is formed by photolithography of a silicon substrate, preferably having a Miller Index of 100, etched with potassium hydroxide. The etched silicon substrate can be repeatedly used as a negative structure or mold, into which is pressed a suitably flowable polymer film, thus forming a positive structure having an array of substantially vertically disposed pillars in the shape of rectangular cuboid-based protrusions with pyramidal tips, as described herein. However, those skilled in the art will recognize that such silicon molds can be quite fragile, which limits their longevity. Thus, in a more preferred embodiment, the silicon mold is first filled with a higher melting/softening temperature polymer material, which is removed to make a positive template. The positive template is then nickel-plated by such methods as nickel electroplating to form a more robust negative template or mold, and the process of making the presently disclosed adhesive structures is conducted using the nickel mold.

More specifically, the method for preparing an adhesive structure according to the present invention comprises introducing a polymer or a polymer precursor to a mold with indentations of micron or sub-micron-dimensions of interest under conditions, e.g., temperatures and pressures, sufficient to permit filling the indentations of the mold by the polymer; cooling the mold and polymer to an extent sufficient to substantially solidify the polymer; releasing pressure on the mold and polymer to provide a molded polymer substrate material comprising protrusions conforming to the indentations of the mold.

In yet another aspect, the present invention relates to a method for preparing an adhesive structure which comprises molding a film or films to a mesh under conditions, e.g., temperatures and pressures, sufficient to permit lamination or welding of the mesh and the films; introducing the mesh/film laminate to a mold with structures or indentations of micron or sub-micron-dimensions of interest under conditions, e.g., temperatures and pressures, sufficient to permit filling the indentations of the mold by the mesh/film laminate; cooling the mold and mesh/film laminate to an extent sufficient to substantially solidify the mesh/film laminate; and releasing pressure on the mold and mesh/film laminate to provide a molded mesh/film laminate substrate material comprising protrusions conforming to the indentations of the mold.

Optimally, this process can be conducted as a single step process, wherein both the film and the mesh are initially associated or aligned, and the film surface is pressed into the mold to form the protrusions, while simultaneously the mesh is pressed against the back-side of the film causing them to laminate or weld together. Such a single step process requires that the film material have a lower softening or melting temperature than the material selected for the mesh. In this way the mesh will not be subjected to temperatures close to its softening/melting point(s) and will remain uncompromised in strength. Accordingly, it is preferable that the difference in melting/softening point(s) temperatures (ΔT) between the mesh material and the film material be at least about 10° C., or even about 20° C., more preferably about 50° C. The single step process provides a big advantage in manufacturing by reducing both time and cost of manufacture.

In still another embodiment, the adhesive structures are integrally molded from a resin selected from at least one of thermoplastic resin, thermosetting resin, and curable resin. By integrally molded is meant that the structure is formed in one piece, including its protrusions, from a mold. For present purposes, thermoplastic resin is a resin that softens when heated and hardens again when cooled. Thermosetting resin is a resin that hardens when heated, cannot be remolded and is deformable from a solid to a liquid. Curable resins are resins that are toughened or hardened by cross-linking of their polymer chains, brought about by chemical additives, ultraviolet radiation, electron beam, and/or heat. In another embodiment, the adhesive structure is at least partially formed by a process selected from nanomolding using a template, polymer self-assembly, lithography, etching, embossing, and roll-to-roll. Preferably, the molding polymer is a thermoplastic polymer, including but not limited to elastomeric polymers.

In yet another embodiment, the two-sided substrate comprises one or more extruded resin layers, such as two or more co-extruded resin layers, each of which resin layer can be the same as or different from another resin layer of the substrate. In still yet another embodiment, the two-sided substrate is derived from a film co-extruded from more than one resin.

In another aspect, a method of making an implant includes assembling a pre-laminate structure having a porous basic structure having a first major surface and a second major surface, an alignment marker overlying the first major surface of the porous basic structure, a first bioabsorbable film overlying the alignment marker and the first major surface of the porous basic structure, and a second bioabsorbable film overlying the second major surface of the porous basic structure, whereby the alignment marker is disposed between the first and second bioabsorbable films. In one embodiment, the method desirably includes applying pressure and heat to the pre-laminate structure to laminate the first and second absorbable films and the alignment marker to the porous basic structure.

As earlier noted, yet another aspect of the invention relates to a method for preparing an adhesive structure which comprises providing a mold via nanomolding techniques including lithography, including indentations of structures of interest; providing a meltable polymer to the mold under conditions sufficient to permit filling the indentations of the mold by the polymer; and treating the mold and polymer to an extent sufficient to substantially solidify the polymer to provide a molded polymer substrate material comprising protrusions conforming to the indentations of the mold. Optionally, this aspect further comprises at least one of the following conditions: wherein the meltable polymer is provided to the mold as a softened film; wherein the polymer is thermoplastic, melt-flowable polymer, e.g., polydioxanone or polyglecaprone 25.

In one embodiment, the molding process is carried out at a temperature ranging from 150 to 220° C., pressure ranging from about 200 to about 11,000 kPa, for a duration of 5 to 30 minutes, and/or at a temperature ranging from 110 to 130° C., pressure ranging from about 200 to about 11,000 kPa, for a duration of 5 to 30 minutes, depending on the melting point of the polymer to be molded.

In yet another embodiment, molding conditions are sufficient to permit filling the indentations of the mold by the polymer and include pressures provided by upper and lower horizontal opposing surfaces, between which surfaces is positioned a space-filling shim surrounding an opening in which are placed from the bottom 1) a first silicon mold layer, 2) a meltable polymer layer, and 3) a second silicon mold layer, and further wherein, 4) an optional protective layer is provided between the lower horizontal opposing surface and the first silicon mold layer and 5) an optional protective layer is provided between the upper horizontal opposing surface and the second silicon mold layer.

To the porous basic structure can be added, at least in part of the area, on both sides, a synthetic, resorbable polymer film, the two polymer films being glued or welded together in pores of the basic structure. As the two polymer films are glued or welded together in pores of the basic structure, the individual layers of the implant according to the invention are reliably connected to each other. Depending on the type of materials used, the polymer films can additionally also be glued or welded to the basic structure.

There are many possibilities for the arrangement of the two opposite-facing films or film pieces. For example, the film pieces need not be congruent. It is also conceivable that several sections are present on the mesh-like porous basic structure in which the porous basic structure is provided with a synthetic, bioabsorbable polymer film on both sides. In a preferred version, at least in a partial area of the porous basic structure, the polymer films are connected over their whole surface to the porous basic structure, or the respective polymer film on the opposite side, but a point-wise connection is also conceivable.

The polymer films can be closed (i.e., without pores) but can also have openings, at least in part of the area. Advantageously, when the films are provided with openings, the entire assembly is rendered more flexible and drapable, and thus more readily conformable to the various intended target tissues to which the adhesive structure is to be applied. In one embodiment, a polymer film is provided which has an array of perforations or through-holes across the surface of and through the thickness of the film. The perforations can be provided by mechanically punching holes through the film or by laser cutting holes through the film, but must be of a diameter or width which will survive the molding process. The perforated film is used as the source of polymer for molding, according to the present invention. Since the presence of the perforations decreases the surface area available for adhesive protrusions, and therefore the total attachment force, the height and diameter of the protrusions can be modified in order to compensate for the loss of protrusions in the perforated areas. Accordingly, the height of the protrusions on a perforated film are advantageously increased relative to a non-perforated film, to between about 400 µm to about 1000 µm, and the widths increased to between about 150 µm to about 250 µm, and relative spacings of about 300 µm to about 500 µm.

An additional advantage of using perforated films in the presently disclosed adhesive structures is that the perforations permit the diffusion of blood away from the wounded area, thus preventing blood accumulation under the adhesive structure.

In order to further increase the flexibility and drapability of the adhesive structures of the present invention, the polymer films, whether perforated or not, can be made from elastomers, including but not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70); elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and epsilon-caprolactone. In another embodiment, the elastomeric copolymer is a copolymer of lactide and epsilon-caprolactone.

In another embodiment the invention is directed to a surgical procedure of applying tissue reinforcing implants, comprising the adhesive structures described above, especially for but not limited to intra-peritoneal or laparoscopic applications, which implants can be fit through a trocar, are simple to deploy, and do not cling to themselves. Alternatively, the adhesive structures can be used during more conventional, open surgical procedures, such as a Lichtenstein repair, a TAPP repair, an onlay repair or a sublay/retromuscular repair. Advantageously the tissue reinforcing implants can be redeployed during a surgical procedure and can be released from the target tissue without causing tissue damage, while having features that retain their tissue adhesion properties.

In another aspect, the implant disclosed herein may be used for repairing abdominal wall defects, such as hernias, especially ventral, incisional, inguinal and umbilical hernias, particularly for intra-peritoneal applications. In one embodiment, the implant may be positioned using laparoscopic techniques for pelvic floor repair and for incontinence treatment. The implant can also be used to repair trocar puncture wounds in the abdominal wall. The mesh-like, porous basic structure provides support to the defect site and is eventually ingrown with tissue and incorporated into the abdominal wall.

In another aspect, the implant is preferably adapted to be folded for passing the implant through a trocar, and then unfolded after passing from a distal end of the trocar. In one embodiment, prior to insertion through the trocar, the implant is preferably rolled up so that marking lines of an alignment marker form the mid-axis of the implant. In one embodiment, the implant may be inserted through a trocar, and after deployment of the implant the alignment marker including the marking lines are used for aligning the implant. In one embodiment, upon deployment of the implant, the marking lines preferably run from cranial to caudal.

Such implants can be suited to use in various applications such as an adjunct to or replacement for sutures and staples used to close surgical incisions, and the implant with said adhesive structures limits damage to the tissue it contacts by having adhesive structures that are optimized to pierce and attach to the tissue but small enough not to damage the tissue, in the event of a necessary removal and redeployment. The implant devices of the present invention can be positioned at a surgical repair site substantially without mechanical fixation of the device, by which we mean that the implant does not require sutures or staples entirely around its periphery, as did prior art devices. However, a relative few or limited number of surgical tacks or sutures can be applied about the periphery of the adhesive structure, if desired, to secure and fixate the device at the tissue defect site. By eliminating the need to thoroughly fixate or secure abdominal wall tissue defects mechanically with sutures or staples, the procedure time is reduced, the patient benefits by having fewer implants (less mass, fewer possible complications, decreased risk of accidentally puncturing an internal organ or blood vessel with a tack or needle and less cost).

And since the procedure time is reduced, there is a reduced likelihood of hospital acquired infection, the patient is under anesthesia for a shorter period of time, and the overall efficiency and safety of the procedure is improved.

It is proposed that pillar-shaped adhesive structures, especially those having rectangular cuboid-based protrusions with pyramidal tips extending from at least one of a planar, areal structure and fabricated from a polymer can provide attachment to tissue under a wide range of surgical site conditions. These structures can penetrate into tissue and grab onto the tissue when an initial force is applied. Due to the shape of the adhesive structures, they then lodge into the tissue and provide attachment, and become difficult to dislodge from the tissue, thereby providing high attachment forces. In some embodiments the attachment forces can be as high as 20 kN/m$^2$, and preferably as high as 50 kN/m$^2$.

In particular, the medical implant is suitable for pelvic floor defects, for repairing a vaginal prolapse, for repairing hernias including inguinal hernias or cicatrical hernias, but also for the treatment of other defects such as abdominal wall closure.

The invention is can be a flexible surgical implant which adapts to the local anatomical conditions, and ensures a secure fit during the surgical intervention and also during the healing process.

In another embodiment, the target surface comprises biological tissue. Although the present invention is not limited by any particular tissue site found in the human body, the implant may be used for a broad range of surgical uses such as urethral repair, pelvic floor repair, hernia repair, cosmesis and fascia repair, any other soft tissue repair, connective tissue repair, vascular tissue repair, neural tissue repair, and bone tissue repair.

EXAMPLES

Example 1

The aim of this example was to fabricate polypropylene films with protrusions. A silicon mold was obtained using photolithography techniques, having an array of cavities, with 105 microns square base, straight side walls down to 185 microns depth and ending with a sharp pyramidal tip, with another 65 microns depth. This silicon mold was used as a template to imprint polypropylene film of 100 microns thickness, obtained from Ethicon, Inc. of Somerville, N.J., USA. The polypropylene film was pressed into the silicon mold under controlled temperature and pressure (180° C., 60 bars) for 5 minutes, melting the polypropylene and filling up the cavities with straight side walls. The polypropylene polymer and the silicon mold were cooled to 60° C. before removal of pressure, after which the polymer structures were de-molded and released by peeling the film away from the silicon mold.

Example 2

Using the same method as set forth in Example 1, protrusions were fabricated on another polymer, a polydioxanone film of 100 microns thickness, obtained from Ethicon, Inc. of Somerville, N.J., USA. The polydioxanone film was pressed into the mold at 120° C., 60 bars for 5 minutes and subsequently cooled to 60° C., before removal of pressure. The polydioxanone polymer was annealed in a vacuum oven at 70° C. for 3 hours, after which the polymer structures were de-molded and released by peeling the film away from the silicon mold.

Example 3

Using the same method as set forth in Example 1, protrusions were fabricated on yet another polymer, a polyglecaprone 25 film of 100 microns thickness, obtained from Ethicon, Inc. of Somerville, N.J., USA. The polyglecaprone 25 film was pressed into the mold at 185° C., 60 bars for 5 minutes and subsequently cooled to 60° C. before removal of pressure. The polyglecaprone 25 polymer was annealed in a vacuum oven at 110° C. for 3 hours, after which the polymer structures were de-molded and released by peeling the film away from the silicon mold.

Example 4

The aim of this example was to fabricate polypropylene films with protrusions having serrated features on the sidewalls. A silicon mold was obtained using photolithography techniques, having an array of cavities, with 105 microns square base, serrated side walls produced with a fast Bosch DRIE process, down to 110 microns depth and ending with a sharp pyramidal tip, with another 70 microns depth. This silicon mold was used as a template to imprint polypropylene film of 100 microns thickness, which was pressed into the silicon mold under controlled temperature and pressure (180° C., 60 bars) for 5 minutes, melting the polypropylene and filling up the cavities with scallop side walls. The polypropylene polymer and the silicon mold were cooled to 60° C. before removal of pressure, after which the polymer structures were de-molded and released by peeling the film away from the silicon mold.

Example 5

Using the same method as set forth in Example 4, serrated protrusions were fabricated on another polymer, a polydioxanone film of 100 microns thickness, which was pressed into the mold at 120° C., 60 bars for 5 minutes and subsequently cooled to 60° C., before removal of pressure. The polydioxanone polymer was annealed in a vacuum oven at 70° C. for 3 hours, after which the polymer structures were de-molded and released by peeling the film away from the silicon mold.

Example 6

Using the same method as set forth in Example 4, serrated protrusions were fabricated on yet another polymer, a polyglecaprone 25 film of 100 microns thickness, which was pressed into the mold at 185° C., 60 bars for 5 minutes and subsequently cooled to 60° C. before removal of pressure. The polyglecaprone 25 polymer was annealed in a vacuum oven at 110° C. for 3 hours, after which the polymer structures were de-molded and released by peeling the film away from the silicon mold.

Example 7

The aim of this example was to fabricate a polypropylene mesh laminate with a polydioxanone film having protrusions as obtained from Examples 1 and 4. The polypropylene mesh was prepared as follows. Ultrapro® mesh is a mesh composed of polypropylene and polyglecaprone 25 filaments. The polyglecaprone 25 filaments were removed from the Ultrapro® mesh by immersing it in Phosphate Buffered Saline (PBS) at 37° C. for one week.

The resulting polypropylene mesh was placed on top of a polydioxanone film of 100 microns thickness, which was pressed into the silicon mold in a single-step process under controlled temperature and pressure (120° C., 60 bars) for 5 minutes, melting the polydioxanone and filling up the cavities. At the same time, the polypropylene mesh was laminated on top of the polydioxanone polymer. The polydioxanone polymer and the silicon mold were cooled to 60° C. before removal of pressure, and the polymer was annealed in a vacuum oven at 70° C. for 3 hours, after which the polymer structures were de-molded and released by peeling the film away from the silicon mold. The final film obtained was a polypropylene mesh laminated with polydioxanone protrusions on a single side.

FIGS. 2A and 2B depict scanning electron microscope images of the resulting polypropylene mesh laminated with polydioxanone straight wall protrusions, and FIGS. 3A and 3B depict polypropylene mesh laminated with polydioxanone serrated wall protrusions.

Using the same method, a polypropylene mesh can be laminated on both sides with polydioxanone protrusions by pressing a silicon mold, a polydioxanone film, a polypropylene mesh, another polydioxanone film and another silicon mold together under controlled temperature and pressure. After annealing and releasing the polymers from both molds, a polypropylene mesh laminated with polydioxanone protrusions on both sides can be obtained.

Example 8

The aim of this example was to fabricate a polypropylene mesh laminate with polyglecaprone 25 protrusions as obtained from Examples 1 and 4. A polyglecaprone 25 film of 100 microns thickness was pressed into the silicon mold under controlled temperature and pressure (185° C., 60 bars) for 5 minutes, melting the polyglecaprone 25 and filling up the cavities. The polyglecaprone 25 polymer and the silicon mold were cooled to 60° C. before removal of pressure. With the polyglecaprone 25 polymer still embedded in the silicon mold, a polydioxanone film of 25 microns thickness, obtained from Ethicon, Inc. of Somerville, N.J., USA, was placed on top of the polyglecaprone 25 and a polypropylene mesh as described in Example 7 was placed on top of the polydioxanone film and pressed together under controlled temperature and pressure (120° C., 10 bars) for 5 minutes, melting the polydioxanone polymer and laminating the polypropylene mesh together with the polyglecaprone 25 film. The polymers were cooled to 60° C. before removal of pressure and annealed in a vacuum oven at 100° C. for 3 hours, after which the polymer structures were de-molded and released by peeling the film away from the silicon mold. The final film obtained was a polypropylene mesh laminated with polyglecaprone 25 protrusions on a single side, using a thin polydioxanone film as the binding agent.

Depending on the type of mold used, the protrusions can have straight or serrated side walls as shown in Examples 1 and 4. Using the same method, a polypropylene mesh can be laminated on both sides with polyglecaprone 25 protrusions by pressing a silicon mold embedded with Monocryl polymer, a thin polydioxanone film, a polypropylene mesh, another polydioxanone film and another silicon mold embedded with polyglecaprone 25 polymer together under controlled temperature and pressure. After annealing and releasing the polymers from both molds, a polypropylene mesh laminated with polyglecaprone 25 protrusions on both sides using polydioxanone films can be obtained.

Example 9

The aim of this example was to develop an accurate and reproducible test method to measure shear attachment forces of the samples to tissue. An Instron mechanical tester (Model: 5565, Instron Corporation, Norwood, Mass.) was used. Corium tissue was obtained from Lampire Biologicals and cleaned in 0.1 N Potassium Hydroxide prior to use. A 100 Newton load cell was assembled to the Instron crosshead and then the slide fixtures were attached to the base of Instron tester. The main power switch of the Instron was turned on and the load cell calibrated. The shear fixture was attached to the load cell. The gauge length and the force reading were zeroed out. The test settings are shown below.

TABLE 1

| Instron Setting | |
| --- | --- |
| Load cell | 10 Newton |
| Crosshead speed | 8 mm/min. |
| Specimen Width | 10 mm |
| Data Acquisition Rate | 10 ms |
| Force calculation | Average user-selected points. |

Sample Preparation

Figure 5:
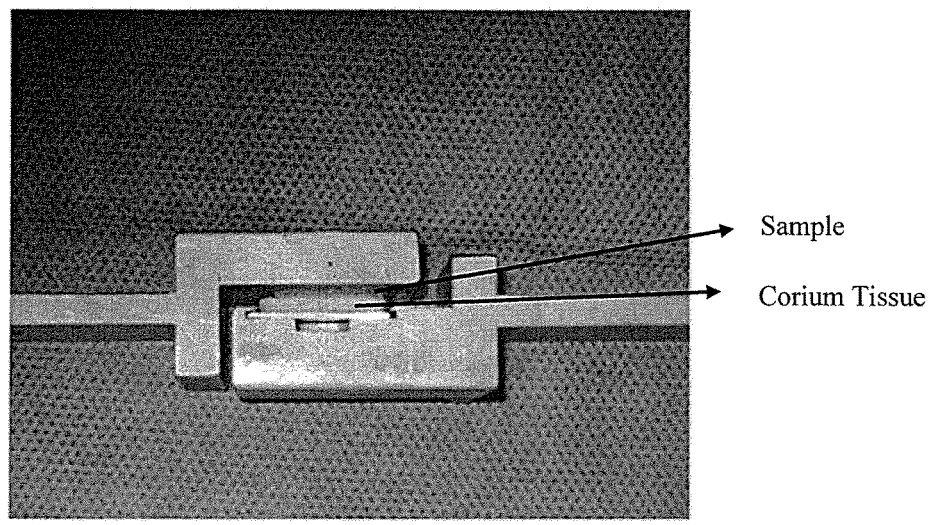
FIG. 5 depicts a fixture for contacting a test sample with Corium Tissue for shear adhesion testing.

Corium tissue was cut using corium die and placed in saline. The alignment fixture was assembled and the cut corium was attached to the lower half of shear testing fixture using super glue and the test material was attached to the upper half shear testing fixture using double sided tape. Then the lower and upper shear testing fixtures were aligned in the alignment fixture (FIG. 5). The assembled alignment fixture was placed with shear testing fixture on the dwell stand with weights for predetermined time.

Test Procedure

Figure 6:
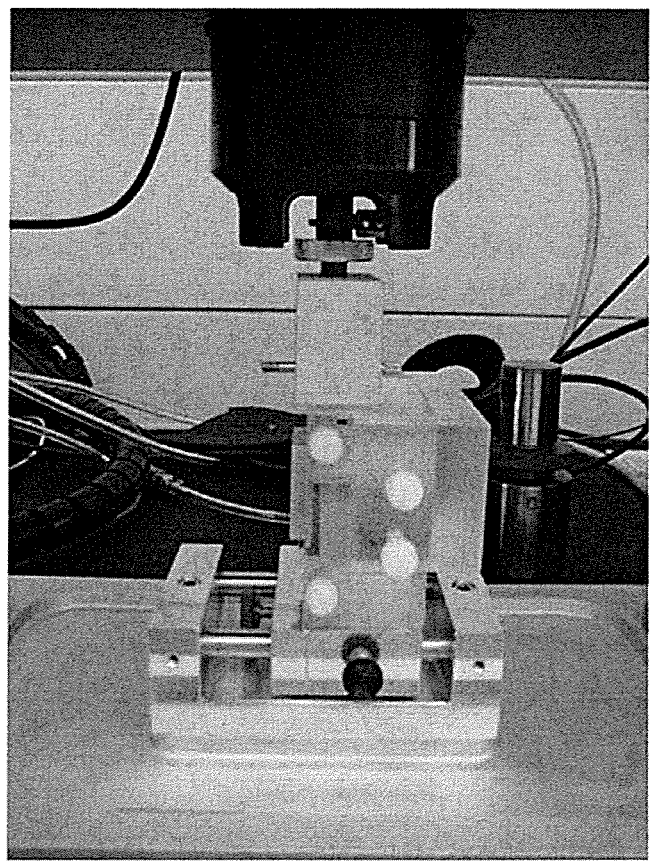
FIG. 6 depicts the fixture of FIG. 5 mounted in Instron equipment for shear testing.
Figure 7:
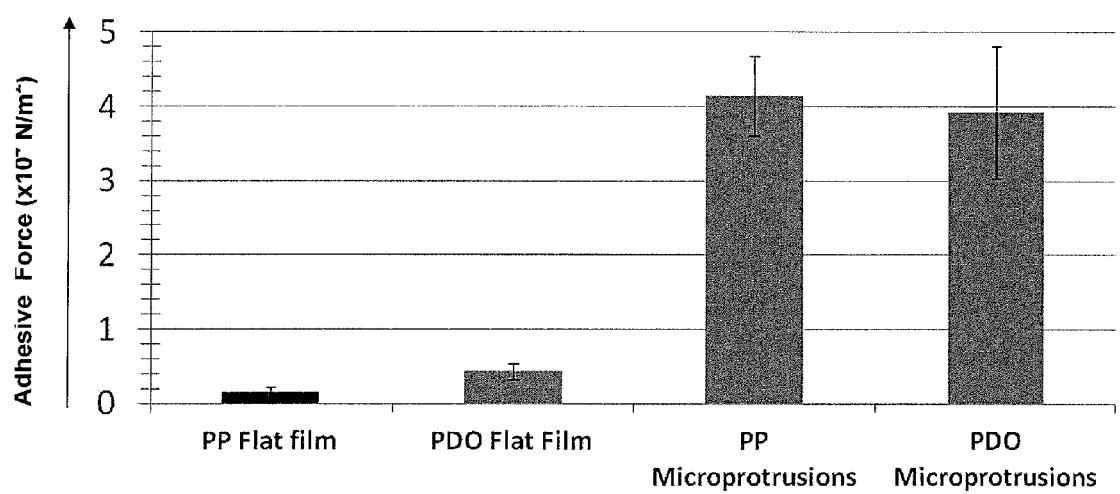
FIG. 7 shows the shear adhesion values of the adhesive structures of the present invention having polypropylene and polydioxanone protrusions as compared with flat films.
Figure 8:
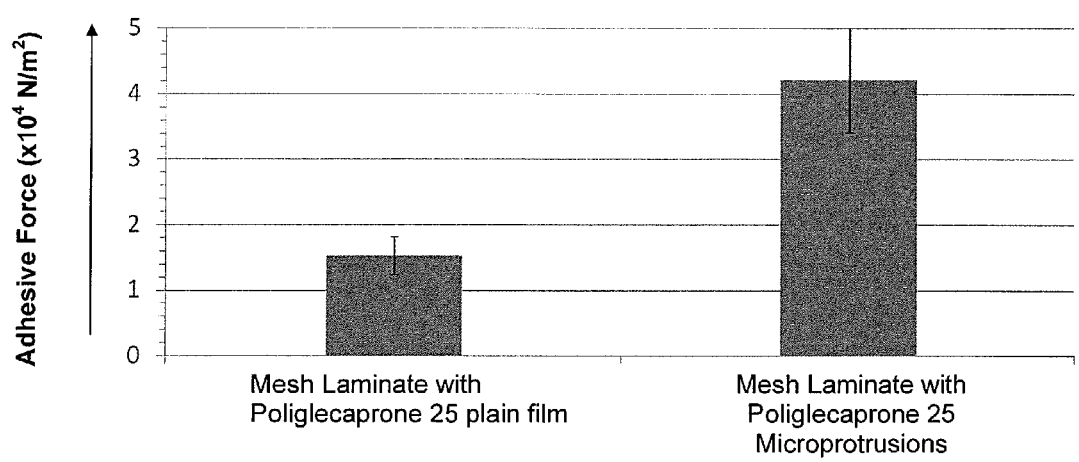
FIG. 8 shows the shear adhesion values of the adhesive structures of the present invention having a polypropylene mesh laminated with polyglecaprone 25 protrusions as compared to polypropylene mesh laminated with polyglecaprone 25 film.
Figure 9:
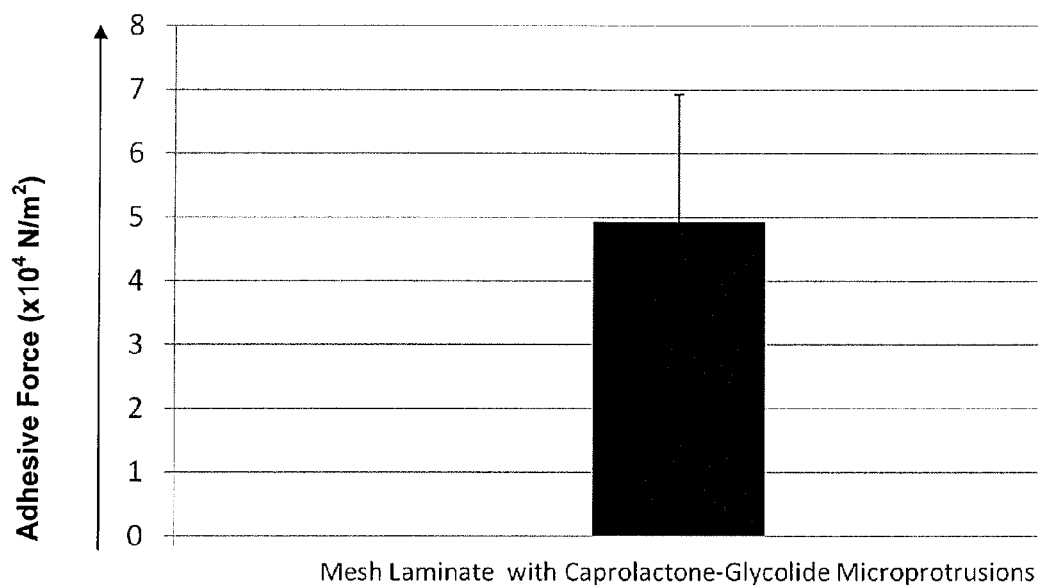
FIG. 9 shows the shear adhesion values of the adhesive structures of the present invention having a polypropylene mesh laminated with a film having elastomeric caprolactone-glycolide protrusions.

The test fixture (FIG. 6) was placed in the Instron and tightened. The fixture attached to the load cell was lowered and aligned with the upper half of shear testing fixture and a pin was inserted to hold it in place. The alignment fixture was removed by loosening top screw first. The balance was set to zero and test started. The test was stopped after peak load was reached. The shear fixture was removed and the cross head returned to original position. The cursor was used to select the peak point from the graph. The next sample was loaded and testing proceeded. The testing data is provided in graphic form in FIGS. 7 and 8, which demonstrate the increased adhesion of the adhesive structures of the present invention, as compared to flat film containing structures of the same polymers.

Example 10

A patient requiring a surgical procedure to repair a hernia defect is prepped and anesthetized for surgery. A small, suitably-located incision is made in the patient's abdominal wall, and a trocar is fed into the incision, such that the end thereof is close to the hernia defect. An adhesive structure having a reinforcing mesh according to the present invention is rolled into a tubular shape and inserted into the patient's abdominal cavity through the trocar. Once inside, the adhesive structure is unrolled into an areal shape, and is firmly pressed against the intraperitoneal wall to cause it to adhere to the location of the defect. The trocar is withdrawn and the incision closed.

Example 11

The aim of this example was to fabricate a polypropylene mesh laminate with an elastomeric caprolactone-glycolide (36/64) film having protrusions using a single step process. The polypropylene mesh was prepared as follows. Ultrapro® mesh is a mesh composed of polypropylene and polyglecaprone 25 filaments. The polyglecaprone 25 filaments were removed from the Ultrapro® mesh by immersing it in phosphate buffered saline (PBS) at 37° C. for one week. The resulting polypropylene mesh was placed on top of a caprolactone-glycolide (36/64) film of 150 microns thickness, which was pressed into the silicon mold under controlled temperature and pressure (121° C., 10 bars) for 5 minutes, melting the caprolactone-glycolide (36/64) and filling up the cavities. At the same time, the polypropylene mesh was laminated on top of the caprolactone-glycolide (36/64) polymer. The caprolactone-glycolide (36/64) polymer and the silicon mold were cooled to 38° C. before removal of pressure, after which the polymer structures were de-molded and released by peeling the film away from the silicon mold. The final film obtained was a polypropylene mesh laminated with caprolactone-glycolide (36/64) protrusions on a single side.

These samples were tested as per the procedure listed in Example 9. The data is shown in Table 2, below. This shows that the shear adhesion is comparable to the samples made in Example 8.

TABLE 2

| Structure | Adhesion Force ($\times 10^4$ N/m$^2$) |
|---|---|
| Mesh Laminate with high aspect ratio pillars of Poliglecaprone 25 | 0.32 |
| Mesh Laminate with Poliglecaprone 25 Microprotrusions | 4.23 |

All patents, test procedures, and other documents cited herein, including priority documents, are fully incorporated by reference to the extent such disclosure is not inconsistent and for all jurisdictions in which such incorporation is permitted. When numerical lower limits and numerical upper limits are listed herein, ranges from any lower limit to any upper limit are contemplated.

Without further elaboration, it is believed that one skilled in the art can, using the preceding description, utilize the present invention to its fullest extent. While the present invention has been described and illustrated by reference to particular embodiments and examples, those of ordinary skill in the art will appreciate that the invention lends itself to variations not necessarily illustrated herein. For this reason, then, reference should be made solely to the appended claims for purposes of determining the true scope of the invention.

We claim:

1. An adhesive structure comprising a planar surface having two sides and a plurality of rectangular cuboid-based protrusions having pyramidal tips, said protrusions extending from at least one of said sides, wherein the protrusions extend substantially normal to the planar surface, and wherein faces of said rectangular cuboid-based protrusions are serrated.

2. The adhesive structure of claim 1, wherein the protrusions extend within +/−10 degrees of normal to the planar surface.

3. The adhesive structure of claim 1, wherein the protrusions have aspect ratios, measured as the ratio of height/width, of at least about 0.5.

4. The adhesive structure of claim 3, wherein the protrusions have aspect ratios from about 1 to 5.

5. The adhesive structure of claim 1, wherein the rectangular cuboid bases of said protrusions are substantially square in horizontal cross-section and the pyramidal tips are square pyramids extending from said rectangular cuboid bases.

6. The adhesive structure of claim 5, wherein the rectangular cuboid bases of said protrusions have widths from about 1 to 500 microns, the pyramidal tips have an included angle of about 54 degrees, and the protrusions have heights greater than or equal to about 0.5 micron.

7. The adhesive structure of claim 1, wherein the planar surface is a polymeric film and the protrusions are integral with said film.

8. The adhesive structure of claim 7, wherein the polymeric film is an elastomer film.

9. The adhesive structure of claim 7, wherein the polymer of said polymeric film and protrusions is a biodurable polymer or a bioabsorbable polymer.

10. The adhesive structure of claim 9, wherein the polymer is a bioabsorbable polymer.

11. The adhesive structure of claim 7, wherein the film has a thickness from about 20 microns to about 200 microns.

12. The adhesive structure of claim 1, wherein said protrusions extend from both sides of said planar surface.

13. The adhesive structure of claim 1, further comprising a porous basic structure laminated to the side of said planar surface opposite said protrusions.

14. The adhesive structure of claim 13, further comprising a second planar surface having two sides with rectangular cuboid-based protrusions having pyramidal tips extending therefrom, laminated to said porous basic structure such that said protrusions extend from both sides of said structure.

15. The adhesive structure of claim 13, wherein said porous basic structure is made from a biodurable polymer and said planar surface and protrusions are made from a bioabsorbable polymer.

16. The adhesive structure of claim 1, having a density of protrusions from the surface thereof from about 400 to about 20,000 protrusions/cm$^2$.

17. The adhesive structure of claim 1, further comprising an adhesion barrier laminated to said porous basic structure on the side opposite said adhesive structure.

18. A surgical procedure comprising:
inserting into a patient at a surgical repair site an implant comprising an adhesive structure comprising a planar surface having two sides and a plurality of rectangular cuboid-based protrusions having pyramidal tips and serrated faces, said protrusions extending substantially normal to the planar surface from at least one of said sides;
approximating edges of the surgical repair site; and
pressing said adhesive structure against the surgical repair site.

19. The surgical procedure of claim 18, wherein the surgical repair is a urethral repair.

20. The surgical procedure of claim 18, wherein the surgical repair is a pelvic floor repair.

21. The surgical procedure of claim 18, wherein the surgical repair is a cosmesis.

22. The surgical procedure of claim 18, wherein the surgical repair is a fascia repair.

23. The surgical procedure of claim 18, wherein the surgical repair is a connective tissue repair.

24. The surgical procedure of claim 18, wherein the surgical repair is a vascular tissue repair.

25. The surgical procedure of claim 18, wherein the surgical repair is a neural tissue repair.

26. The surgical procedure of claim 18, wherein the surgical repair is a bone tissue repair.

27. The surgical procedure of claim 18, wherein the surgical repair is an abdominal wall incision.

28. The surgical procedure of claim 18, wherein the surgical repair is a hernia.

29. A surgical procedure comprising:
   inserting into a patient at a surgical repair site an implant comprising an adhesive structure comprising a planar surface having two sides and a plurality of rectangular cuboid-based protrusions having pyramidal tips and serrated faces, said protrusions extending substantially normal to the planar surface from at least one of said sides;
   approximating edges of the surgical repair site; and
   pressing said adhesive structure against the surgical repair site substantially without mechanical fixation of the device.

30. The surgical procedure of claim 29, further comprising removing and repositioning the implant without damaging tissue surrounding the surgical repair site.

31. The surgical procedure of claim 29, wherein said adhesive structure provides an adhesion force of from about 20 kN/m$^2$ to about 50 kN/m$^2$ to said surgical repair site.

* * * * *